United States Patent
Weigl et al.

(10) Patent No.: US 6,743,399 B1
(45) Date of Patent: Jun. 1, 2004

(54) PUMPLESS MICROFLUIDICS

(75) Inventors: Bernhard H. Weigl, Seattle, WA (US); Clinton L. Williams, Seattle, WA (US); Jon W. Hayenga, Redmond, WA (US); Ronald L. Bardell, Redmond, WA (US); Thomas E. Schulte, Redmond, WA (US)

(73) Assignee: Micronics, Inc., Redmond, WA (US)

( * ) Notice: Subject to any disclaimer, the term of this patent is extended or adjusted under 35 U.S.C. 154(b) by 0 days.

(21) Appl. No.: 09/684,094

(22) Filed: Oct. 6, 2000

Related U.S. Application Data

(63) Continuation-in-part of application No. 09/415,404, filed on Oct. 8, 1999.
(60) Provisional application No. 60/213,865, filed on Jun. 23, 2000.

(51) Int. Cl.$^7$ .................................................. B02L 3/00
(52) U.S. Cl. ..................... 422/102; 422/68.1; 422/99; 422/100; 436/174; 436/179; 436/180
(58) Field of Search .................. 422/61, 68.1, 99–102, 422/55, 58; 436/164, 165, 169, 174, 178, 180; 435/283.1, 287.1, 287.7, 287.8, 288.3; 204/400

(56) References Cited

U.S. PATENT DOCUMENTS

| | | | |
|---|---|---|---|
| 4,426,451 A | 1/1984 | Columbus | |
| 4,676,274 A | 6/1987 | Brown | |
| 4,849,340 A | 7/1989 | Oberhardt | |
| 5,204,525 A | 4/1993 | Hillman | |
| 5,225,163 A | 7/1993 | Andrews | |
| 5,248,479 A | * 9/1993 | Parsons et al. | 422/58 |
| 5,716,852 A | * 2/1998 | Yager et al. | 436/172 |
| 5,842,787 A | 12/1998 | Kopf-Sill et al. | |
| 5,856,174 A | * 1/1999 | Lipshutz et al. | 435/286.5 |
| 5,876,187 A | 3/1999 | Forster et al. | |
| 5,876,675 A | 3/1999 | Kennedy | |
| 5,922,591 A | * 7/1999 | Anderson et al. | 435/287.2 |
| 5,928,194 A | 7/1999 | Maget | |
| 5,932,799 A | 8/1999 | Moles | |
| 5,948,684 A | * 9/1999 | Weigl et al. | 436/52 |
| 5,972,710 A | * 10/1999 | Weigl et al. | 436/34 |
| 5,974,867 A | * 11/1999 | Forster et al. | 73/61.41 |
| 5,992,820 A | 11/1999 | Fare et al. | |
| 6,007,775 A | * 12/1999 | Yager | 422/57 |
| 6,043,080 A | 3/2000 | Lipshutz et al. | |
| 6,086,825 A | 7/2000 | Sundberg et al. | |
| 6,130,098 A | 10/2000 | Handique et al. | |
| 6,134,950 A | * 10/2000 | Forster et al. | 73/54.01 |
| 6,136,272 A | * 10/2000 | Weigl et al. | 422/82.05 |
| 6,143,248 A | * 11/2000 | Kellogg et al. | 422/72 |
| 6,171,865 B1 | * 1/2001 | Weigl et al. | 204/453 |
| 6,277,641 B1 | * 8/2001 | Yager | 436/52 |
| 6,296,020 B1 | 10/2001 | McNeely et al. | |

FOREIGN PATENT DOCUMENTS

| | | |
|---|---|---|
| EP | 0381501 A | 8/1990 |
| EP | 0430248 A | 6/1991 |
| WO | WO 9317328 A | 9/1993 |
| WO | WO 9706437 A | 2/1997 |
| WO | WO 9807019 A | 2/1998 |
| WO | WO 9855852 A | 12/1998 |
| WO | WO 9917093 A | 4/1999 |
| WO | WO 0022436 A | 4/2000 |

* cited by examiner

Primary Examiner—Lyle A. Alexander
Assistant Examiner—Dwayne Handy
(74) Attorney, Agent, or Firm—Seed IP Law Group PLLC

(57) ABSTRACT

A microfluidic device which operates without the need for an external power source. The device includes a body structure, at least one microscale channel within the structure, a port for introducing fluid into the channel, and a power source internal to the structure for propelling the fluid through the channel. Various structures are described which embody the invention.

3 Claims, 9 Drawing Sheets

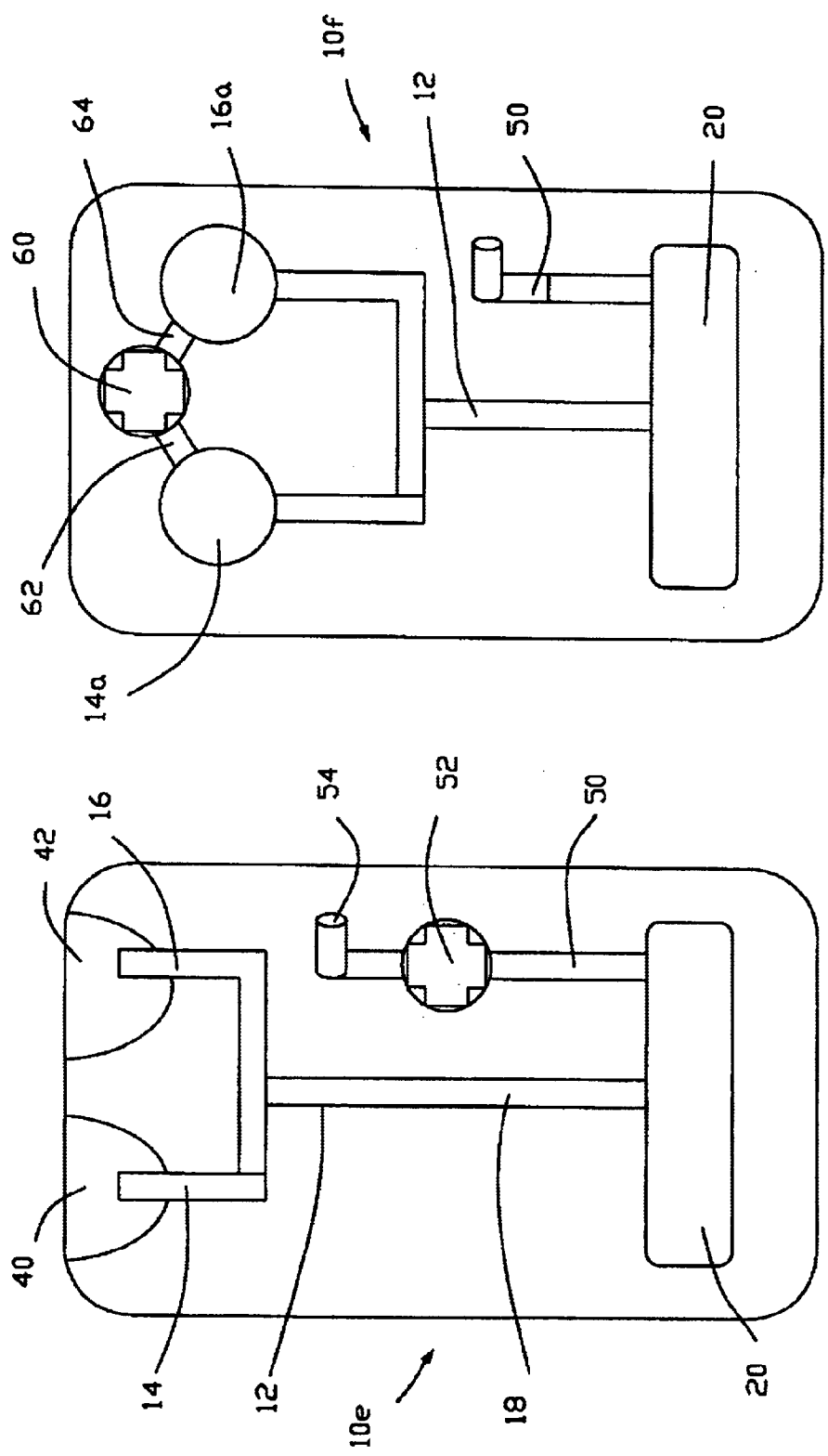

PUMPLESS MICROFLUIDICS

CROSS-REFERENCE TO RELATED APPLICATIONS

This patent application is a continuation-in-part application of U.S. patent application Ser. No. 09/415,404, filed Oct. 8, 1999, and also of U.S. Provisional Patent Application Serial No. 60/213,865, filed Jun. 23, 2000 which applications are incorporated herein in their entirety by reference.

BACKGROUND OF THE INVENTION

1. Field of Invention

This invention relates generally to microfluidic systems, and, in particular, to a microfluidic device in which the operation is conducted entirely without the benefit of an external fluidic driver.

2. Description of the Prior Art

Microfluidic devices have become very popular in recent years for performing analytical testing. Using tools developed by the semiconductor industry to miniaturize electronics, it has become possible to fabricate intricate fluid systems which can be inexpensively mass produced. Systems have been developed to perform a variety of analytical techniques for the acquisition and processing of information.

U.S. Pat. No. 5,716,852 is an example of such a device. This patent teaches a microfluidic system for detecting the presence of analyte particles in a sample stream using a laminar flow channel having at least two input channels which provide an indicator stream and a sample stream, where the laminar flow channel has a depth sufficiently small to allow laminar flow of the streams and length sufficient to allow diffusion of particles of the analyte into the indicator stream to form a detection area, and having an outlet out of the channel to form a single mixed stream. This device, which is known as a T-sensor, allows the movement of different fluidic layers next to each other within a channel without mixing other than by diffusion.

Microfluidic systems of this type require some type of external fluidic driver, such as piezoelectric pumps, microsyringe pumps, electroosmotic pumps and the like, to operate. It would be desirable, in many situations, to produce a device which is entirely driven by a readily available force, such as gravity, capillary action, absorption in porous materials, chemically induced pressures or vacuums (e.g., by a reaction of water with a drying agent), or by vacuum and pressure generated by simple manual action, rather than by an external fluidic driver requiring a separate power source having moving parts. Such a device could be extremely simple to operate, could be manufactured very inexpensively, and could be used to perform many diagnostic assays using a variety of microfluidic methods.

SUMMARY OF THE INVENTION

Accordingly, it is an object of the present invention to provide a microfluidic device which can be operating without a fluid driver that requires a power source.

It is a further object of the present invention to provide a low cost disposable qualitative assay which can be adapted to medical or environmental uses, among others.

It is still a further object of the present invention to provide a simple microfluidic system which can perform analytical functions without the necessity of an external electrical or mechanical fluid driver system.

These and other objects are accomplished in the present invention by a simple cartridge device containing microfluidic channels which perform a variety of analytical techniques for the acquisition of information without the use of any electrical or mechanical driving forces applied to the cartridge. The cartridge may be constructed from a single material, such as plastic, by conventional manufacturing methods, such as injection molding, to create a low cost device which can be discarded after a single use. Inherently available forces such as gravity, hydrostatic pressure, capillary force, absorptive force manually generated pressure, or vacuum, move the fluids through the microfluidic channels to accomplish the desired analytical analyses. Other applications for this technology include toys and advertising devices.

BRIEF DESCRIPTION OF THE DRAWINGS

FIG. 7 is another embodiment of the cartridge of the present invention which is driven by aspiration within the cartridge itself;

FIG. 8 is another embodiment of the cartridge of the present invention which is driven by a chemical process or a pump from within the cartridge;

DETAILED DESCRIPTION OF THE PREFERRED EMBODIMENTS

Figure 1:
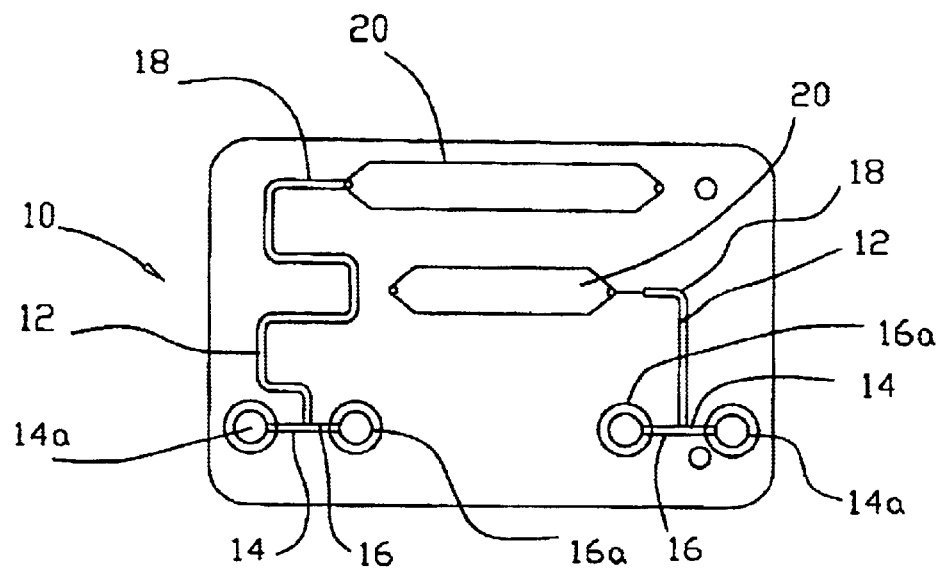
FIG. 1 is a plan view of a microfluidic device manufactured according to the present invention.

Referring now to FIG. 1, there is shown a cartridge generally indicated at 10 containing the elements of the present invention. Note that like parts are given like reference numerals in the embodiments contained in the present application. Cartridge 10 is preferably constructed from a single material, such as plastic, using a method such as injection molding, and is approximately the size and thickness of a typical credit card. Located within cartridge 10 are several flow channel systems 12, preferably comprising T-Sensors which are described in detail in U.S. Pat. No. 5,716,852, which disclosure incorporated by reference herein. Each T-Sensor 12 consists of a first sample channel 14, a second sample channel 16, a common channel 18, and a terminating storage chamber or reservoir 20. At the end of each channel 14, 16 opposite common channel 18 is located a circular input port 14a, 16a respectively, where droplets of reagents and samples can be placed for analysis.

In operation, T-Sensor 12 allows the movement of different fluidic layers next to each other within channel 18 without mixing other than diffusion, as fluids generally show laminar behavior within microfluidic channels. A sample solution placed in port 14a passes through channel 14 and an indicator solution placed in port 16a passes through channel 16, and the streams from channels 14, 16 merge in common channel 18 and flow next to each other until they exit into reservoir 20. Smaller particles such as ions or small proteins diffuse rapidly across the fluid boundaries within channel 18, whereas larger molecules diffuse more slowly. Large particles, such as blood cells, show no significant diffusion within the time the two flow streams are in contact. An interface zone is formed between the fluid layers. The signal strength of a particular optical or electrochemical property, such as fluorescence intensity of the interface zone is a function of the concentration of the analyte. In addition, it is sometimes desirable to add a third stream to T-Sensor 12, with one channel containing a reference stream for analysis purposes. This is described in detail in U.S. Pat. No. 5,948,684, which issued Sep. 7, 1999.

Manually operated microfluidic devices such as T-Sensor 12 can be used to qualitatively or semi-quantitatively determine analyte concentrations. A practical use may be the determination of several parameters directly in whole blood. A color change in the diffusion zone of a T-Sensor detection channel can provide qualitative information about the presence of an analyte. This method can be made semi-quantitative by providing a comparator color chart with which to compare the color of the diffusion zone. This method would work somewhat similar to a paper test strip, but with much better control and reproducibility. In addition, long term monitoring functions can be accomplished by placing such a device in line with a sample feed. With a T-Sensor, assays can be performed directly with whole blood, whereas paperstrip readings can be affected by the color and consistency of whole blood.

The accuracy of this method can be enhanced by combining the device with a readout system which may consist of an absorbance, fluorescence, chemiluminescence, light scatter, or turbidity detector placed so that the detector can observe an optically detectable change which is caused by the presence or absence of a sample analyte or particle in the detection channel. Alternatively, electrodes can be placed within the device to observe electrochemically observable changes caused by the presence or absence of a sample analyte or particle in the in the detection channel.

One embodiment of this device is a disposable cartridge combined with a mass market digital camera-like detector system: a flash would illuminate the sensor area, and any type of optically detectable signal would be interpreted by image processing software and yield a chemical concentration or count output.

Figure 2:
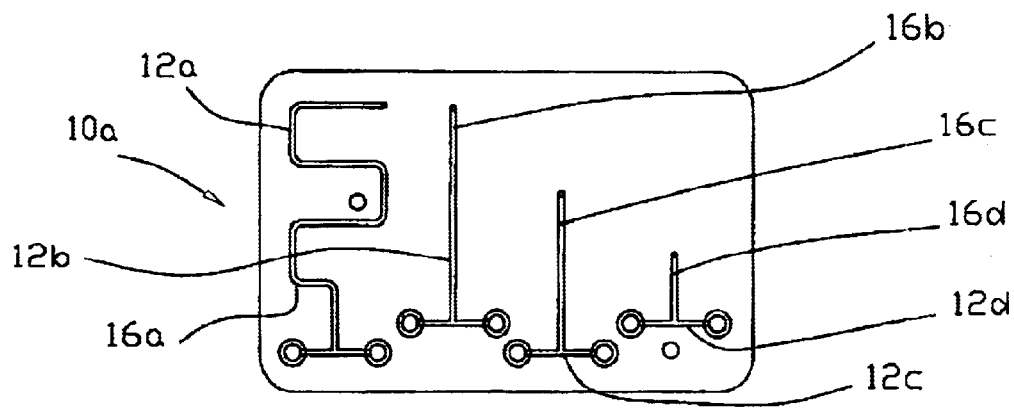
FIG. 2 is a plan view depicting an alternative embodiment of the cartridge of FIG. 1.

FIG. 2 shows an alternative embodiment for cartridge 10 of FIG. 1. Note that in the various embodiments, similar elements have been given similar numerals. Cartridge 10a contains four separate T-Sensor circuits 12a, 12b, 12c, 12d. These T-Sensors include common channels 16a, 16b, 16c, 16d having different configurations.

Figure 3:
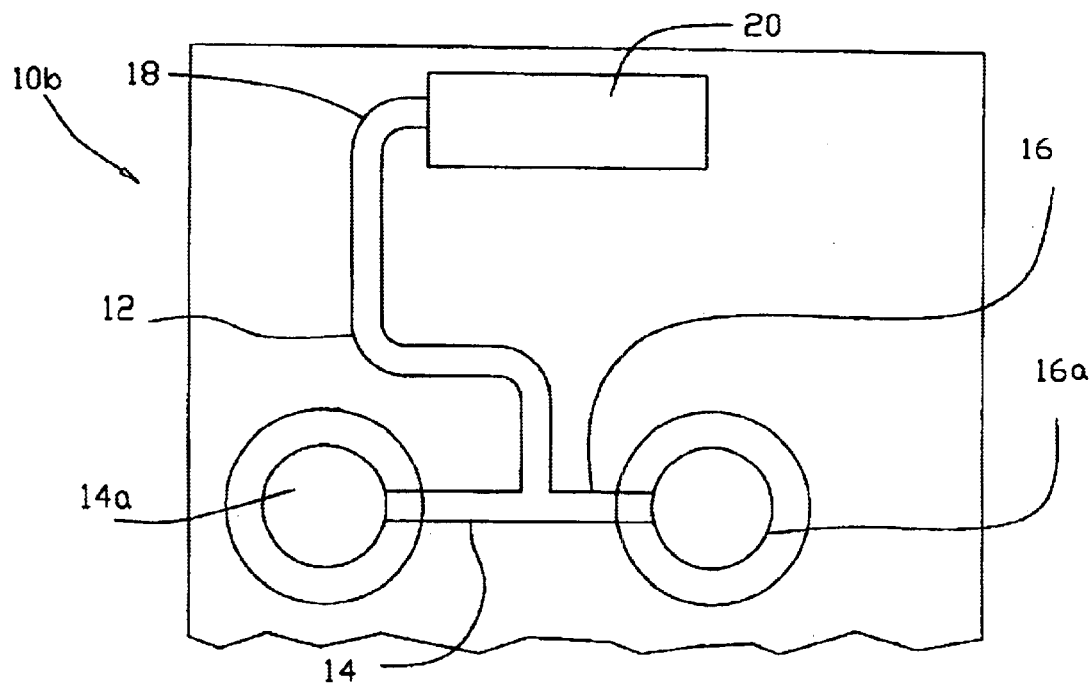
FIG. 3 is another alternative embodiment of the cartridge of the present invention which is driven by absorption.

The driving force for operating cartridges such as those shown in FIGS. 1 and 2 is generally supplied from an external source. U.S. patent application Ser. No. 09/080,691, which was filed on May 18, 1998, the disclosure of which is hereby incorporated by reference in its entirety, is an example of a device which requires external motive forces to operate properly. Various syringe pumps located external to the cartridge are coupled to the device for operation. FIG. 3, however, shows a device which uses an internal force to drive the circuitry.

Figure 4:
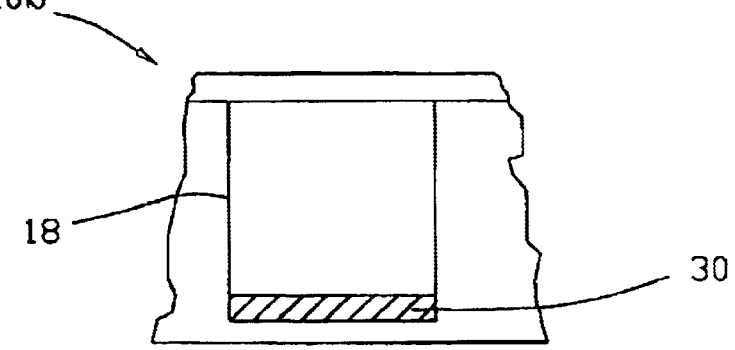
FIG. 4 is a sectional view taken along lines 4—4 of FIG. 3.

Turning now to FIG. 3, there is shown a T-Sensor 12 within cartridge 10b, substantially similar to that taught in FIG. 1. Channels 14, 16 intersect to form common channel 18 which terminates in reservoir 20. Input ports 14a, 16a are connected to channels 14, 16 respectively at the ends opposite channel 18. A porous absorbent material 30 is positioned within channels 14, 16, 18 and reservoir 20 of cartridge 10b, as can be clearly seen in FIG. 4. To operate the T-Sensor of FIG. 3, a liquid sample of reagent is applied to port 14a while a liquid sample of a specimen is applied to port 16a. Material 30 acts to propel the liquids through channels 14, 16, 18 into reservoir 20. Material 30 is preferably an absorbent hydrophilic substance such as cellulose, calcium chloride, calcium sulfate, or silica gel.

Figure 11:
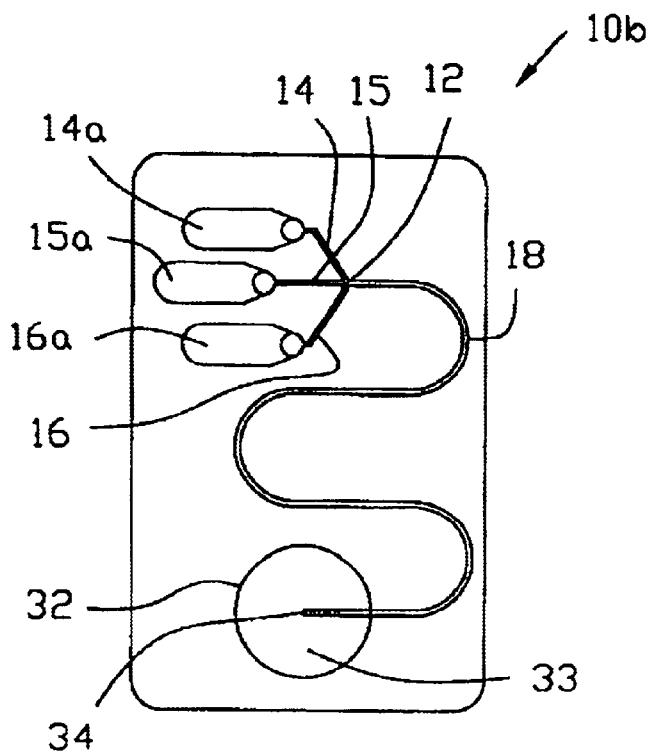
FIG. 11 is another embodiment of the cartridge of FIG. 3 which is driven by absorption.

FIG. 11 shows another embodiment of a cartridge using the absorption principles of the present invention. Referring now to FIG. 11, cartridge 10b uses a T-Sensor like device 12 having three input ports 14a, 15a, 16a coupled to channels 14, 15, 16 which converge to form common channel 18. Channel 18 terminates at a reservoir 32 which contains a circular absorbent material 33. Channel 18 is connected to reservoir 32, and thus material 33, by a series of small apertures 34, which, in the present embodiment, allow a fluid traveling within channel 18 to initially reach the center of circular absorbent material 32. As fluid from channel 18 reaches material 33, material 33 acts to propel fluid through channels 14, 15, 16 and common channel into reservoir 32. In this embodiment, fluid exits from apertures 34 onto the center of material 33 and travels radially at a constant speed toward the outer circumference of circular material 33, thus providing a constant flow speed within channel 18 as the fluid is absorbed by material 33. The absorption begins at the center of material 33, and expands exponentially the amount of absorption front as the absorption spot expands. By varying the shape, geometry, and directional preference of absorbent pad 33, the flow speed of the fluid absorbed by material 33 can be controlled as desired.

Figure 12:
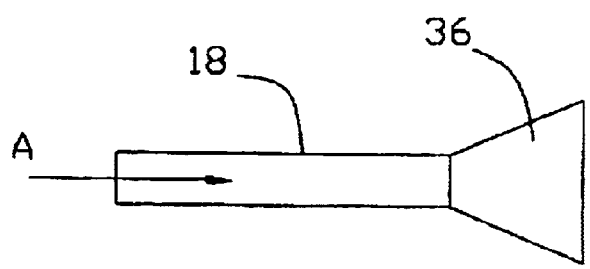
FIG. 12 is an enlarged view of an alternative embodiment of an absorption material for use in the present invention.

FIG. 12 shows an enlarged section of a cartridge using the absorption principles shown in FIG. 11. In this embodiment, common channel 18 terminates in a triangular section 36 of absorbent material. As fluid travels through channel 18 in the direction shown by arrow A, it reaches material 36, and since it is triangularly shaped, the length of the diffusion front is increased as diffusion progresses, thereby compensating for an increase in fluid resistance in material 36 as more fluid must pass through already wetted absorbent material. Other geometries which can be used in the present invention include hyperbolically expanding triangular shapes.

Different shapes may not only be used for both keeping the flow speed constant, but also for increasing or decreasing the flow speed, or for cyclically varying the flow speed. For example, a sinusoidal expanding "triangular" shape can be used to keep the average flow speed constant, but let it vary periodically.

The movement of fluids through cartridge 10b can be enhanced by means of a surface treatment on the walls of channels 14, 15, 16 and 18 formed by contacting the surface with low-pressure plasma. In addition, other features which enhance fluid flow (which will be discussed in greater detail hereinafter), such as capillary forces and gravity feed, can be employed to assist this method.

Another method available for use in cartridge 10b of FIG. 11 is driven by evaporation, where absorbent material 33 is not used, and reservoir 32 is exposed to the atmosphere outside cartridge 10b, where a portion of the fluid from channel 18 evaporates. If the area of fluid that is exposed to atmosphere at the outlet is larger than that at the inlet, then fluid movement will occur in principle. Alternatively, one or both of the outlet or inlet can be cooled or heated, thereby controlling the evaporation rate and, thus, the fluid flow rate and direction, to maintain a constant flow rate or to vary the rate.

According to this method, the device in FIG. 11 can be operated beyond the time at which the absorptive capacity of the absorbent pad is exhausted. Reservoir 32 has a relatively large surface area, causing the evaporation of fluid at a higher rate than the combined areas of inlet reservoirs 14a, 15a, and 16a. This creates a motive force, driving the fluid contained in cartridge 10b towards the apertures 34. In this embodiment, material 33 is not required for the function of this device.

The movement of fluid through a microfluidic cartridge by differential evaporation at the inlet and outlet reservoirs is, provided that all evaporation areas are kept at the same temperature, only a function of the surface area of these evaporation areas. If the surfaces are liquid-filled, then the actual area differences determine the force driving the fluid movement. If the surfaces are a wetted porous material such as a filter paper, then the surface roughness also increases the effective surface area. The rougher a surface is, the more "evaporative force" it creates.

The differential "evaporative force" can be enhanced by keeping the different evaporative areas at different temperatures, as evaporation is enhanced by increased temperature. For example, an inlet area at a low temperature, and an outlet area of the same size as the inlet area, but at a higher temperature, would create fluid movement towards the outlet.

Alternatively, a magnetic material can be placed within reservoir 20, and the liquids applied to ports 14a, 16a comprise ferroflulds which would be propelled through channels 14, 16, 18 by magnetic forces into reservoir 20. These ferrofluids could also be used in combination with reagents and specimen samples to either push or pull these fluids through T-Sensor 12 by magnetic forces.

Figure 5:
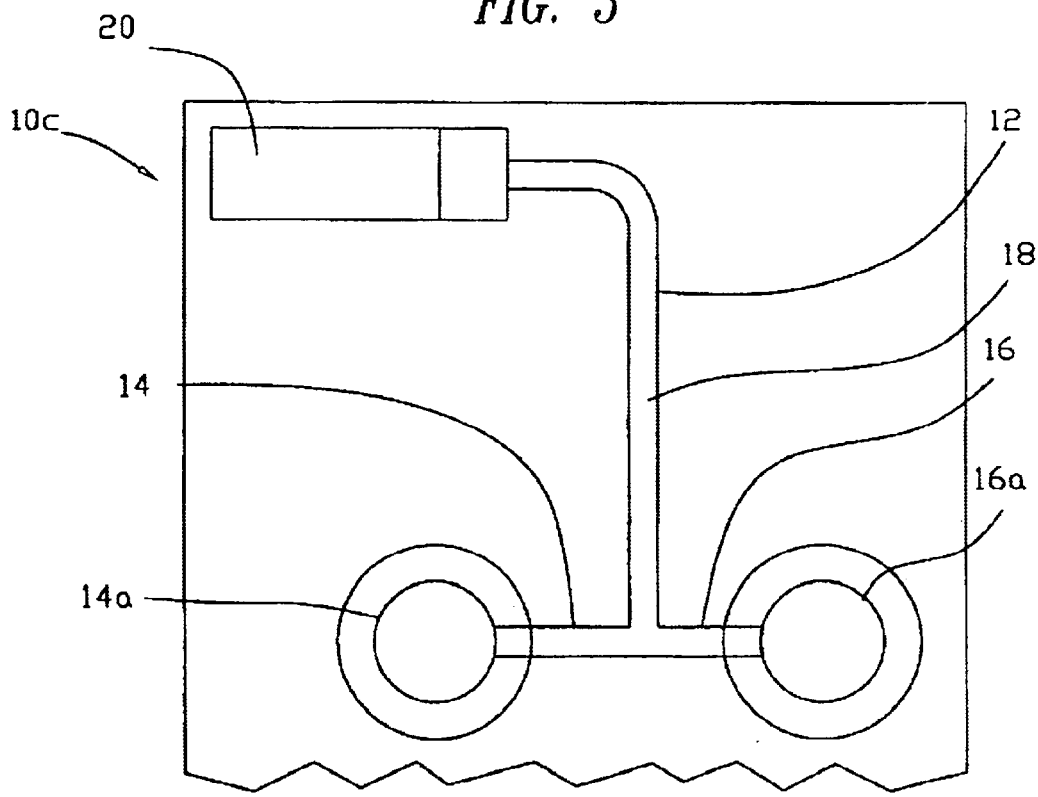
FIG. 5 is another alternative embodiment of the cartridge of the present invention which is driven by capillary action.

FIG. 5 shows another alternative design for operating the T-Sensor of FIG. 1. In this embodiment, a liquid sample of reagent is applied to port 14a of cartridge 10c while a liquid sample of specimen is applied to port 16a. Channels 14, 16, and 18 are sized such that capillary action draws the reagent and specimen through channels 14, 16 and 18 of T-Sensor 12 into terminating reservoir 20. Channels 14, 16, and 18 preferably have dimensions between 10 nanometers and 500 micrometers in width, which act to create capillary action to power T-Sensor 12.

Figure 6:
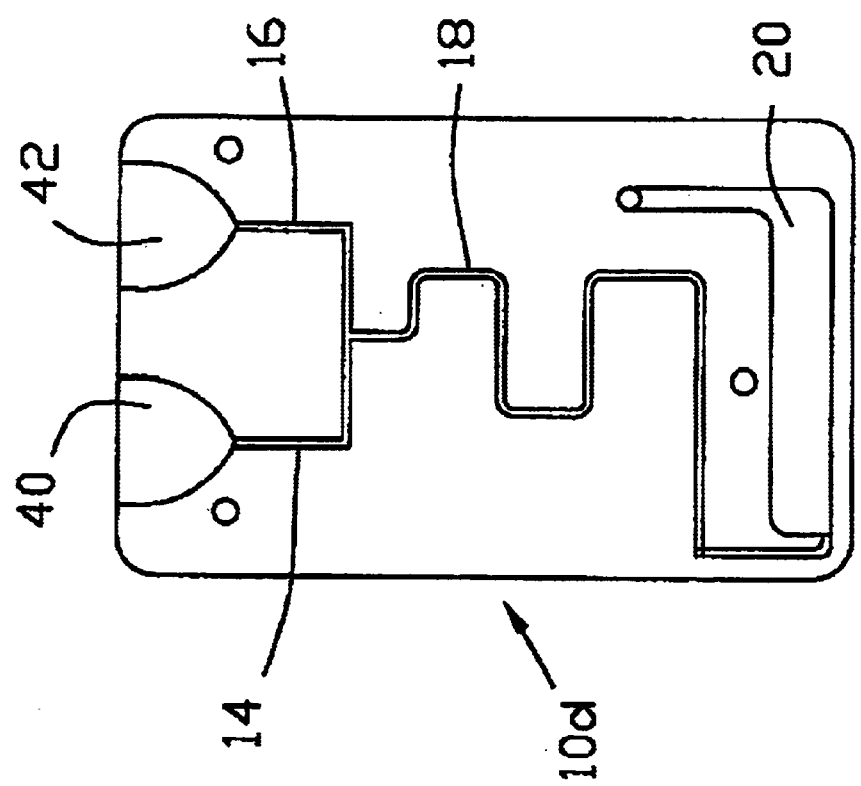
FIG. 6 is another alternative embodiment of the cartridge of the present invention which is driven by hydrostatic pressure.

FIG. 6 is still another alternative embodiment for T-Sensor operation. In this cartridge 10d, T-Sensor 12 includes a first pressure head 40 for receiving a reagent sample and a second pressure head 42 for receiving a specimen sample. To operate T-Sensor 12, the cartridge is placed vertically and a sample of reagent is introduced into channel 14 via head 40 and a sample of specimen introduced into channel 16 via head 42. The hydrostatic pressure present by virtue of the orientation of cartridge 10d drives the liquids through channel 18 of T-Sensor 12 and into reservoir 20. The velocity at which the liquids travel through cartridge 10d can be varied by tilting the cartridge from the vertical position.

Figure 13:
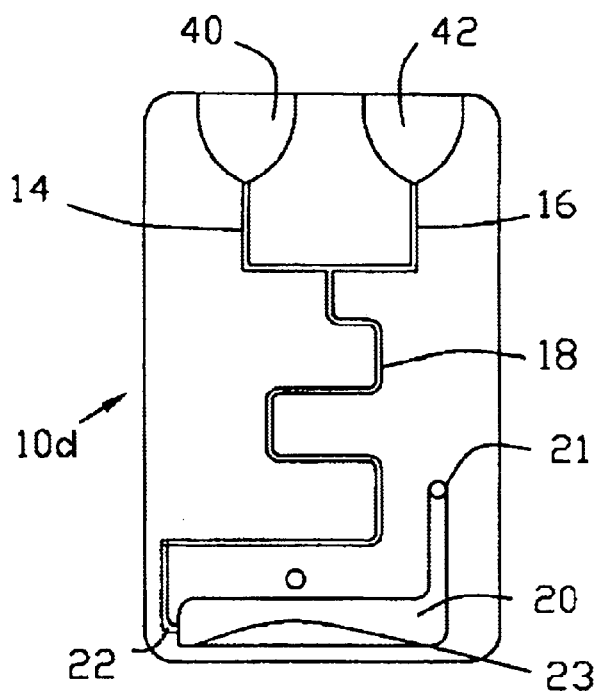
FIG. 13 is another embodiment of the cartridge of the present invention exhibiting improved fluid flow within the cartridge.

The flow of fluids within cartridge 10d of FIG. 6 can be significantly enhanced using a structural feature that uses the reservoir edges to improve the "wet-out" of the cartridge. Referring now to FIG. 13, cartridge 10d includes pressure heads 40 and 42 which are coupled to channels 14 and 16 respectively, which flow into common channel 18. Channel 18 eventually connects to a reservoir 20, which is preferably vented to the atmosphere external to cartridge 10d via a venting aperture 21. Connection 22 between channel 18 and reservoir 20 is a right angle bend which is located at some distance from bottom wall section 23 and reservoir 20.

Figure 14:
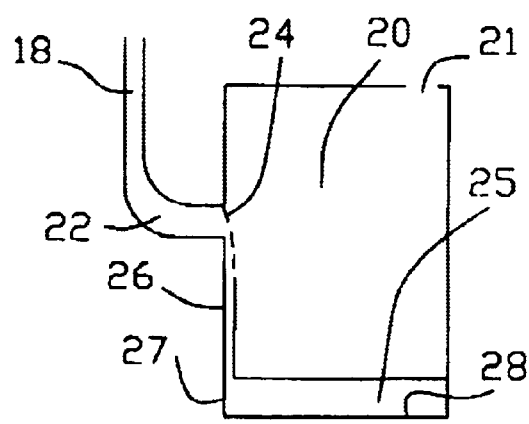
FIG. 14 is an enlarged view of a portion of the cartridge of FIG. 13.

FIG. 14 is an enlarged view of the connection between channel 18 and reservoir 20. While the horizontal dimension of the channel mouth at connection 22 may be narrow or wide, vertical dimension 24 must be large enough that the surface tension of a liquid 25 flowing with channel 18 is inadequate to support a liquid drop, if this requirement is fulfilled within the structure of cartridge 10d, the liquid 25 entering reservoir forms a thin stream as shown at 26 from the bottom of connection 22 and flows down the wall 27 of reservoir 20. By using this structure, pressure oscillations in channel 18 that would occur as drops form and fall within reservoir 20 is avoided, thus ensuring a smooth liquid flow.

Hydrostatically driven microfluidic circuits use gravity as their driving force. The pressure generated is a function of the difference in inlet and outlet liquid height level. This pressure is a constant for a given height difference, and generates a fluid flow in the microfluidic circuit. Flow speed and flow ratios for a given pressure are largely a function of the fluid resistance in these microchannels, and of the viscosity of the solutions. For example, in a given T-Sensor, the fluid flow ratio between the two fluids will depend on the viscosity ratio of the two fluids. Blood has a viscosity about 3–4.5 times greater than that of aqueous solutions. Therefore, blood will flow more slowly than an aqueous solution as the two streams flow along each other in a T-sensor channel. However, for a given hydrostatic pressure, the dividing line between the two streams will remain independent of a change of viscosity (i.e., for the same hydrostatic pressure, the dividing line will be at the center of the channel). The volumes that flow through the channel per time however, are a function of their viscosity, and higher viscosity solutions will flow at a lower volume flow rate. This will eventually cause the water levels of the two inlet streams to become different, since the low-viscosity fluid will drain more quickly. This change in water levels between the two inlet streams then would have an effect on the hydrostatic pressure, and the resulting flow patterns. This can easily be remedied by using comparably large volume pressure heads which change very little during the measurement time.

This phenomenon is different from flow patterns in a volume-controlled flow situation (as is usual for syringe-pump positive displacement pumps). In this case, a constant volume flow rate will move the same amount of liquid per time through the channel. In case of different viscosities of sample and reagent, the center line will shift to the side of the lower-viscosity stream, as the higher viscosity stream flows more slowly.

The advantages of pressure driven flow in T-Sensors is therefore that the position of the center line is independent of viscosity. This phenomenon can be used to simplify detection in these devices.

One method to compensate for a change in flow speed due to a change in viscosity is to include a small "metering bubble" in the inlet channels. The time it takes to fill this bubble is proportional to the flow speed of each solution, which again is proportional to the viscosity of each solution.

While hydrostatic pressure is a very constant source of power for microfluidic structures, it may be necessary at times for some types of structures to overcome some initial surface effects while filling a cartridge prior to allowing gravity or capillary forces to keep the flow constant and well controlled. A variety of methods for "jump-starting" the flow can be used: tapping on the inlets, using a syringe to either aspirate or press fluid into the disposable, using a "bubble pump", or a variety of other processes.

Microfluidic cartridges can also be surface-treated (for example, by a so-called Oxygen Plasma process) to create surfaces that can be more easily wetted by aqueous solutions. Such cartridges generally do not need to be "jump-started", as the capillary forces draw fluids into these cartridges autonomously. By selective surface treatment, some areas of the cartridge can be filled, while others can create so-called surface tension valves, which require a certain amount of pressure to overcome before they wet.

An alternate embodiment of the cartridge of FIG. 6 is shown in FIG. 7. In this cartridge 10e, a vent passage 50 is connected to reservoir 20. Vent passage 50 includes a compressible aspiration bubble pump 52 and a closure means 54. To operate T-Sensor 12 in cartridge 10e, aspiration bubble 52 is depressed while a reagent sample and a specimen sample are introduced into pressure heads 40,42. After pressure heads 40,42 are filled, closure means 54 is activated to seal vent passage 50 from atmosphere. Bubble 52 is then released causing the reagent and specimen to enter T-Sensor 12 via channels 14, 16 and 18 and into reservoir 20.

FIG. 8 shows yet another version of the cartridge of the present invention. Cartridge 10f contains a compressible pressure bubble 60 which is connected to ports 14a and 16a via passages 62, 64 respectively, while vent passage 50 connects reservoir 20 to atmosphere. T-Sensor 12 in cartridge 10f operates as follows: bubble 60 is depressed, forcing air through passages 62, 64, and consequently causing reagent in port 14a and specimen in port 16a to enter T-Sensor 12 via channels 14, 16 and 18 and into reservoir 20.

Bubble 60 can alternatively contain a liquid in equilibrium with its gas phase; some liquids, such as alcohol, acetone, methanol, have a vapor pressure high enough at room temperature to provide a constant pressure source to drive liquids through T-Sensor 12. The pressure source will only cease once all the liquid in bubble 60 has been converted to the gas phase; until then, pressure will be constant, and only a function of temperature.

Another type of microfluidic device which can be readily adapted to manual operation is the H-Filter. The H-Filter structure is described in detail in U.S. Pat. No. 5,932,100, the disclosure of which is hereby incorporated by reference. Manually operated H-Filters can be used to separate components from particulateladen samples such as whole blood, or to manufacture small quantities of chemicals.

Figure 9:
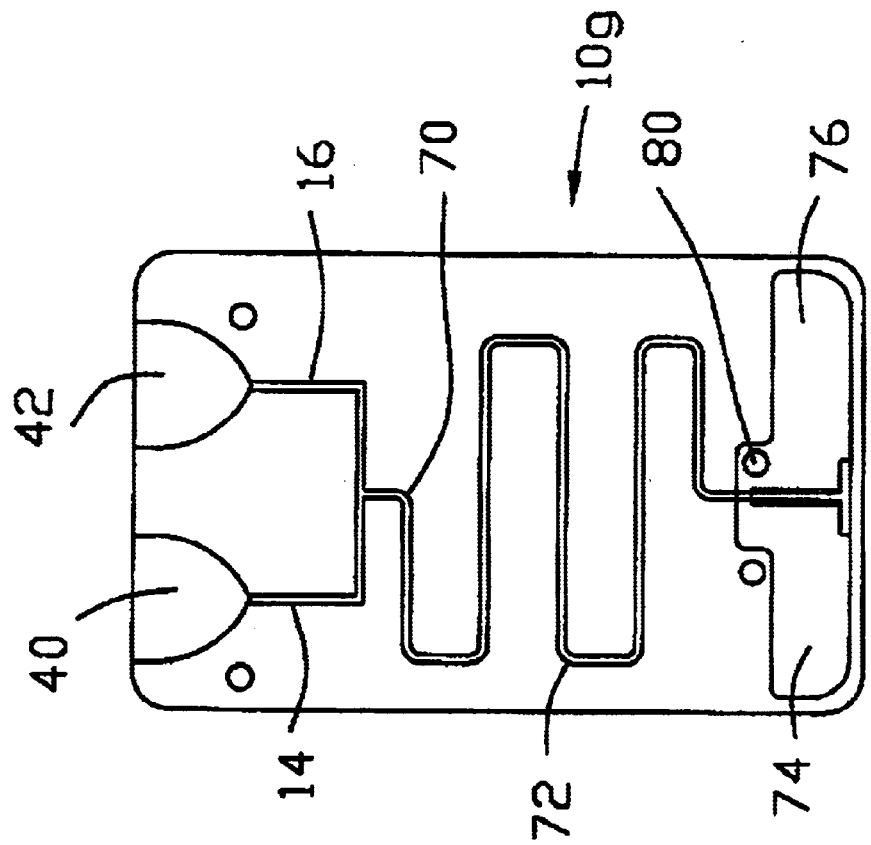
FIG. 9 is another embodiment of the cartridge shown in FIG. 6 having an H-Filter within the cartridge.

FIG. 9 shows a cartridge similar to FIG. 6 embodying the present invention in the form of an H-Filter. Cartridge log contains a first pressure head 40 for receiving a reagent sample and a second pressure head 42 for receiving a specimen sample. An H-Filter 70 is coupled to pressure heads 40, 42 via channels 14, 16 respectively. H-Filter 70 consists of a channel 72 which connects channels 14, 16 to a pair of separate reservoirs 74, 76, which are connected only through a common vent 80. In the embodiment shown in FIG. 9, channel 72 of H-Filter 70 follows a serpentine path which assists in creating turbulence to enhance mixing; however, channel 72 can be straight, such as channel 16c shown in T-Sensor 12c in FIG. 2.

Referring now to FIG. 9, the operation of cartridge 10g will now be described. A sample, such as whole blood, is inserted into pressure head 40, while an acceptor reagent, such as water or saline is inserted into pressure head 42. Two parallel laminar streams will flow through channel 72 as the liquids travel from channels 14, 16. Smaller components of the sample stream will diffuse into the acceptor stream. The two parallel flows are then split up into separate reservoirs 74, 76 at the end of H-Filter 70. Reservoir 74 will then contain a sample solution with a reduced concentration of the extracted component, while reservoir 76 contains the acceptor reagent containing the extracted reagent at a level of some fraction of its original concentration in the sample. The contents of both reservoirs 74, 76 can then be harvested from cartridge 10g for future use, or be processed through further integrated microfluidic structures.

It may be advantageous to provide the disposables prefilled with reagents on the cartridge. Such reagents can be placed in inlet reservoirs, and sealed with a membrane, tape, or the like. Prior to the measurement, the user fills the sample inlet reservoir, and then removes the reagent seal. This process allows the reagents to start flowing down the channel. Alternative sealing methods may be surface-tension controlled orifices which require a certain initial pressure to overcome the surface effects, and to start flowing, or other types of manual or mechanical valves.

By combining a flexible manual "bubble pump" (as shown in FIGS. 7 and 8) with a one-way valve, fluids can be pumped in a closed circuit for a period of time. This may be advantageous when extracting or washing samples or reagents, and multiple passes through a microfluidic structure would increase the yield.

Figure 10:
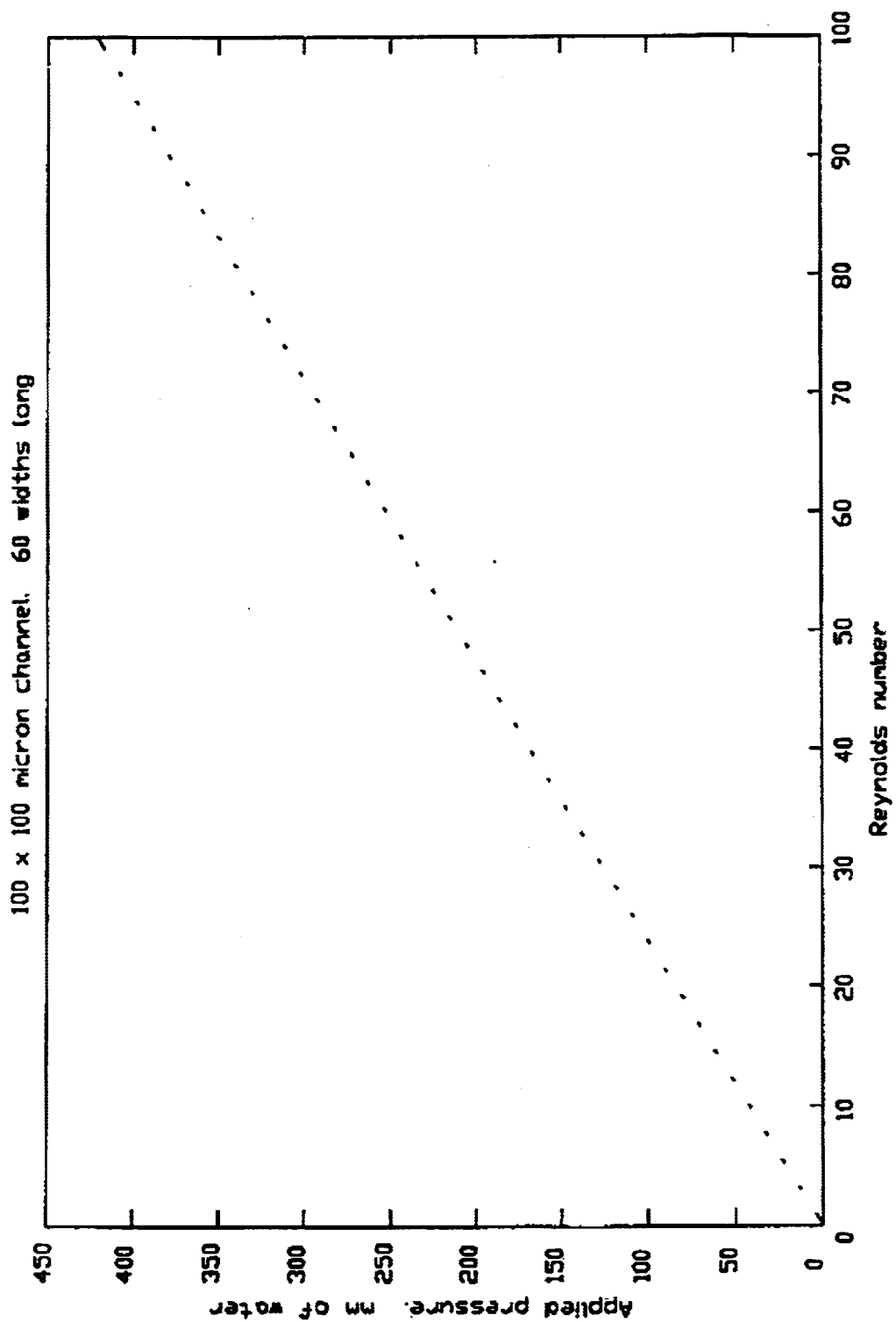
FIG. 10 is a graph showing the relationship between hydrostatic pressure and Reynolds number for a typical microfluidic mixing structure.

Mixing solutions in manually driven microfluidic circuits can be either diffusion-based in a laminar channel (as in H-Filters and T-Sensors), or quasi-turbulent. Several structures can be used to mix solutions in a quasi-turbulent fashion. Generally, such structures consist of a succession of corners, edges, zig-zag channels, or other features which increase the likelihood that laminar recirculation or turbulence can be generated in microchannels at the flow speeds available with a manually driven microfluidic circuit FIG. 10 shows the relationship between hydrostatic pressure and Reynolds number for a typical microfluidic mixing structure. A Reynolds number of 10 is usually sufficient to induce mixing. Turbulent or quasi-turbulent mixing is required for relatively large particles (Molecular weight of 1000 KD or more). Alternatively, bubble pumps can generate enough pressure to turbulently mix solutions in most microfluidic structures.

Other assay methods that lend themselves to manually driven microfluidic circuits are assays that use agglutination or sedimentation. For example, antibody-antigen complexes may either sediment into a microfluidic reservoir for detection or further processing, or they may form particles that intentionally get stuck in small microfluidic features such as orifices. The presence or absence of these complexes in particular parts of the microstructures can serve as an indicator for the presence, absence, or quantity of an analyte. This could be used to develop a method for blood typing.

Figure 15:
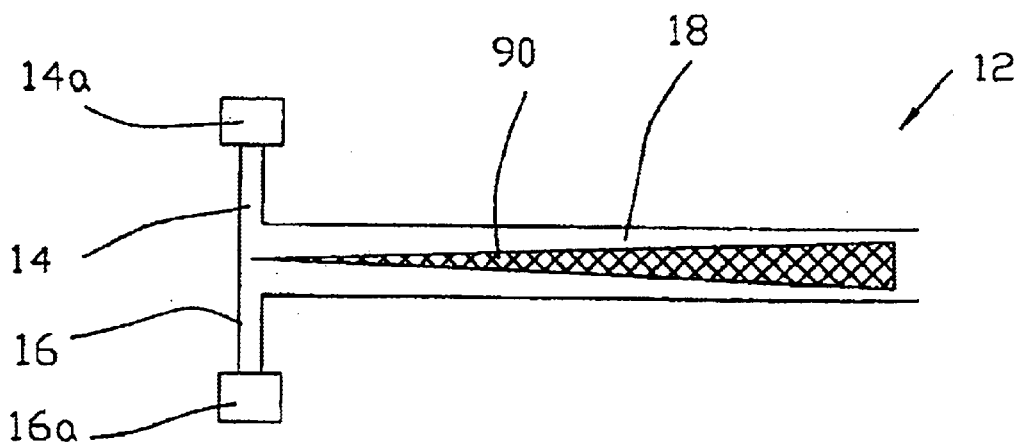
FIG. 15 is a graphic representation of a T-Sensor for use in the present invention.
Figure 16:
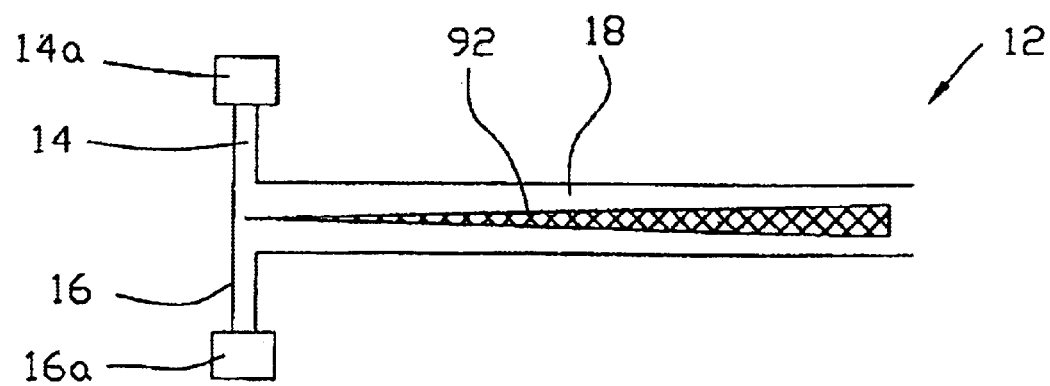
FIG. 16 is a graphic representation similar to FIG. 15 showing a T-Sensor using different analytes.
Figure 17:
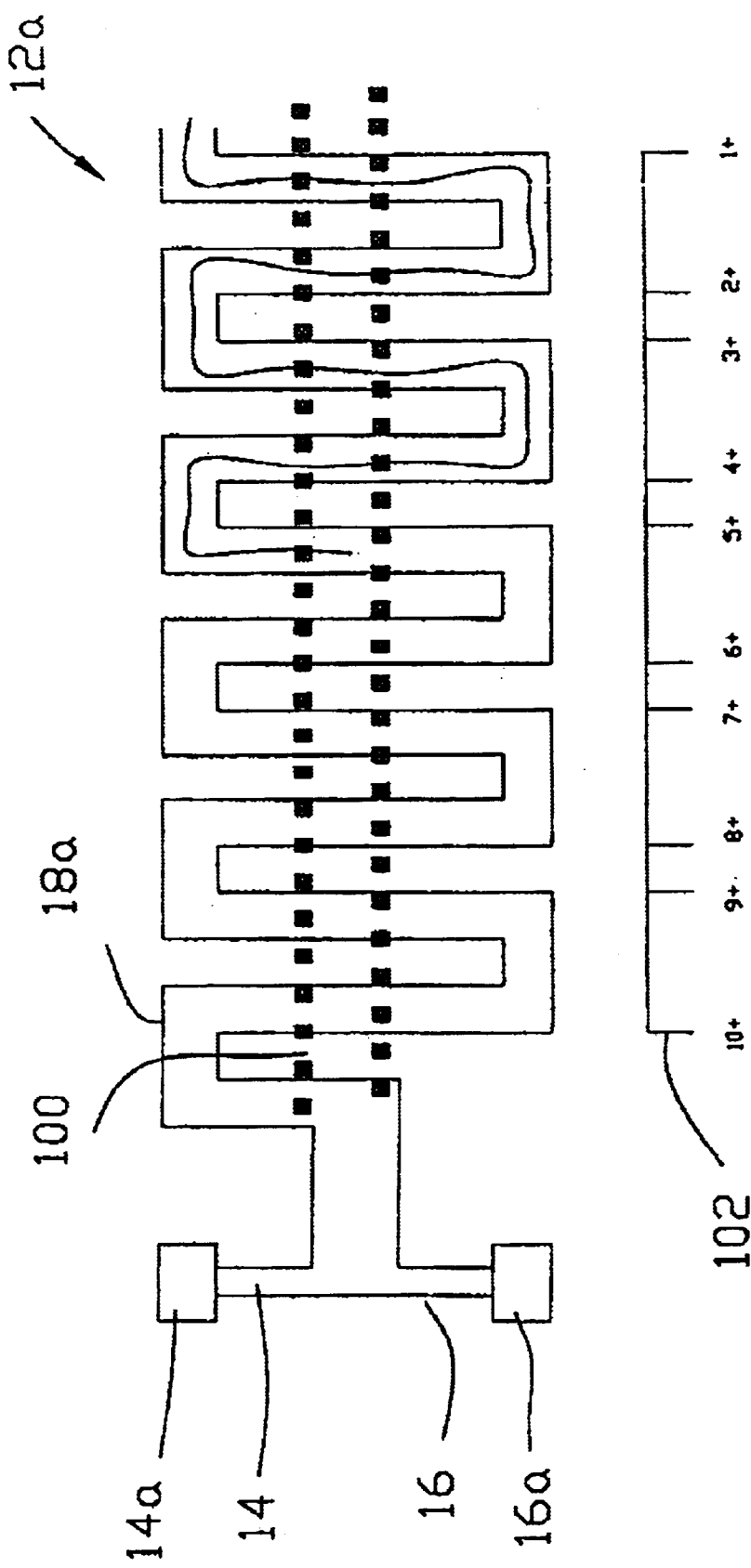
FIG. 17 is a graphic representation of a T-Sensor using a readout device according to the present invention.

A simple detection method for analyzing the results of an assay performed in a microfluidic format according to the present invention is shown in FIGS. 15–17. Referring now to FIG. 15, a basic T-Sensor device 12 is shown having an indicator port 14a and an analyte port 16a. Port 14a is connected to main channel 18 by a sample channel 14, while port 16a is connected to channel 18 by an analyte channel 16. In FIG. 15, a high concentration analyte is loaded into port 16a, and when T-Sensor 12 is operated with an indicator solution within port 14a, a diffusion pattern forms as shown at 90. In FIG. 16, a low concentration analyte is loaded into port 16a, and a different diffusion pattern 92 is generated.

At some point along channel 18, the reaction between the analyte and indicator will become sufficiently intense to be seen visually. This point in channel 18, which is located some distance from channels 14 and 16, will correlate with a particular concentration of analyte within channel 18. Optical aids, such as a magnifying lens, colored filter layer, or slit may aid in the manual visual interpretation of the concentration.

An example of a device for simple quantitation of a microfluidic device which requires no external instruments is shown in FIG. 17. Referring now to FIG. 17, a convoluted T-Sensor 12e having ports 14a, 16a and channels 14, 16 contains a main channel 18a upon which a viewing window 100 has been inserted. In addition, a chart 102 is placed near T-Sensor 12e which contains indicia representative of different concentrations of the desired analyte. During operation of T-Sensor 12e, quantitation is achieved by interpreting the point at which visible reaction has occurred at the interface between the sample and indicator. The only portion of channel 18a visible is seen through viewing window 100. In this embodiment the analyte may be at a 4+ to 5+ amount (1+ being low, 10+ being high) because in the 6+ view area of window 100, there is barely an reaction visible This embodiment is aimed at providing a quantitative assessment of analyte concentration in a format that is compatible with manual performance and visual readout. This format is particularly appropriate for use with kinetic assays—in which product builds up with time—since time in a microfluidic channel corresponds to geographic distance. Examples of kinetic assays are enzyme assays, and some slow finding reactions, such as some antibody-antigen reaction. However, this technique may also work with "fast" reactions, because visual interpretation incorporates both intensity of color and "thickness" of color at the interface.

Figure 18:
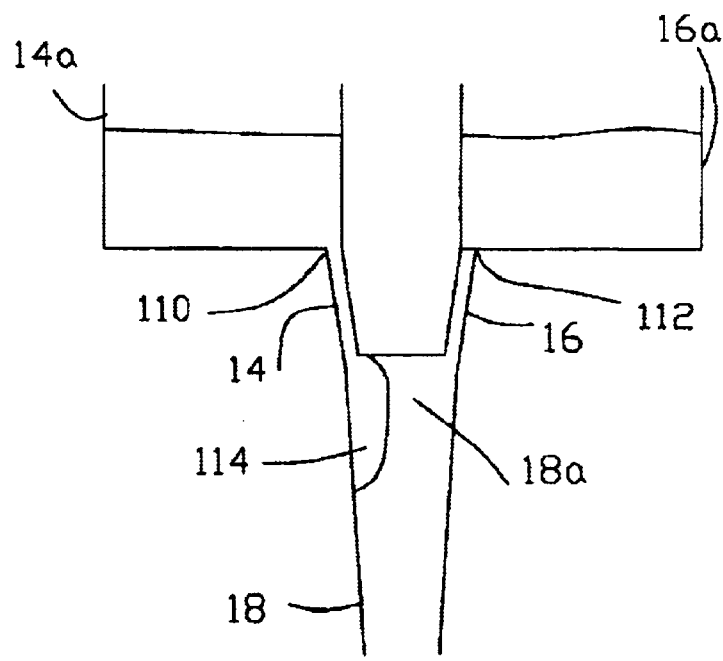
FIG. 18 is a fragmentary view of a microfluidic channel joining two reservoirs in a Y-junction constructed according to the present invention.

FIG. 18 shows a microfluidic device according to the present invention which joins two fluid streams in a manner which prevents the formation of air bubbles within the channels that may hamper the performance of the device. Referring now to FIG. 18, a pair of reservoirs 14a, 16a are coupled to a main microfluidic outlet channel 18 by a pair of inlet channels 14, 16 respectively. In this embodiment, channel 18 is tapered such that it is wider at section 18a where it connects to channels 14, 16. Channel 14 connects to reservoir 14a at 110, while channel 16 connects to reservoir 16a at 112.

When reservoirs 14a, 16a are initially filled, a geometry of channels 14, 16 and 18 make it difficult to avoid trapping an air bubble within channel 18, because typically the liquid in one channel flows in section 18a of channel 18 before the liquid in the other channel breaks through the surface tension barrier where the channel meets the bottom of the reservoir. As shown in FIG. 18, fluid from reservoir 14a has already reached channel 18, as shown at 114, whereas the fluid in reservoir 16a is still trapped by the surface tension of the liquid-gas interface where reservoir 16a meets channel 16, as shown at 112.

To avoid trapping an air bubble in this microfluidic device, two constraints must be addressed in the design of the microfluidic circuitry. First, the outlet channel 18 must be large enough to contain the volume of inlet channel 14 from reservoir 14a without trapping the air in channel 16. Second, the pressure differential between the pressure in outlet channel 18 and the pressure at 110, which is due to the fluid resistance to flow within channel 14, must be greater than the pressure differential between the pressure in outlet channel 18 and the pressure at 112, which is due to the surface tension of the gas-liquid interface at 112. This is accomplished by narrowing the width of channel 16 as needed for the surface tension characteristic of the liquid and gas pair.

Surface tension valves are based on the difference in resistance contained in unwetted orifice as compared to a wetted orifice. These valves are considered "single use" valves, as once they are wetted, they behave essentially like a low in resistance flow channel (dynamic resistance); however, these valves present enough resistance (static resistance) to block the fluid flow, even if some force is applied to them such as pressure, capillary forces, or hydrostatic pressure. Once this static force is overcome by a "breaking force," fluid will flow through the valve.

Resistance of the inlet channels 14, 16, however, is only dynamic resistance. The more the inlet channels are filled, the higher the resistance (provided that there are no capillary forces to drive fluids through these inlet channels).

In operation, as the cartridge is being filled, only the resistance of one of the inlet channels 14, 16 becomes higher than the static resistance of the surface tension valve of the other inlet channel, the surface tension valve will break, and fluids from both reservoirs 14a, 16a will flow into outlet channel 18. Surface tension valves typically consist of an orifice, a channel terminating in sharp edges, or other structures which create a high surface tension. Alternatively, the surface of a channel can be coated with a specific material in the valve area, thereby increasing the surface tension resistance at that point. However, the actual resistance exhibited by these valves depends to a large extent on the exact dimensions and surface properties; thus, manufacturing tolerances can have a significant impact on the accuracy of these valves.

One method of improving the reliability of surface tension valves would be to provide multiple redundant surface tension valves in parallel rather than a single valve. Although the multiple valves will vary statistically in resistance, but the average of the group will be close to that of a single valve. For example, by placing multiple small orifices between two channels, the same approximate surface tension can be achieved each time. FIG. 11 shows the use of multiple orifices within a channel to exhibit this principle.

Finally, an alternative design for a surface tension valve would provide a maximum breaking resistance, along with a minimum breaking resistance, for the valve.

The principles of the present invention can be applied to many other types of products. For example, a cartridge containing a microfluidic device as described can be used as science kits, such as a miniature chemical laboratory, for educational purposes. Another use could be as a novelty device that uses fluid flow to visualize specific patterns, such as company logos, names, signatures, and the like on a small plastic card roughly the size of a standard credit card.

While the invention has been shown and described in terms of several preferred embodiments, it will be understood that this invention is not limited to these particular embodiments and that many changes and modifications may be made without departing from the true spirit and scope of the invention as defined in the appended claims.

What is claimed is:

1. A microfluidic device for joining two liquid streams when using gravitational force as a driving source, comprising:

a first reservoir for containing a first liquid, having a first outlet orifice;

a first channel having a first inlet opening coupled to said first orifice and a first outlet opening;

a second reservoir for containing a second liquid, having a second outlet orifice;

a second channel having a second inlet opening coupled to said second orifice and a second outlet opening;

a driving source, comprising gravitational force;

and a main microfluidic channel having an inlet coupling region for coupling said outlet openings of said first and second channels to said main channel, said inlet coupling region having a greater width than said main channel, such that liquid driven by said gravitational force entering said coupling region from one of said first or second reservoirs through said channel outlet openings flows into said main microfluidic channel without trapping an air bubble within said other channel and blocking said outlet opening of said other channel.

2. The device of claim 1, wherein said inlet openings of said first and second channels comprise surface tension valves.

3. The device of claim 2, wherein the static resistance of said surface tension valves is lower than the dynamic resistance within said first and second channels.

* * * * *